United States Patent [19]

Horrobin et al.

[11] Patent Number: 5,128,152
[45] Date of Patent: Jul. 7, 1992

[54] IRON-CONTAINING COMPOSITIONS AND METHOD FOR TREATING CANCER

[75] Inventors: David F. Horrobin, Guildford, England; Michel E. Begin, Nova Scotia, Canada

[73] Assignee: Efamol Limited, Surrey, England

[21] Appl. No.: 711,104

[22] Filed: Jun. 3, 1991

Related U.S. Application Data

[63] Continuation of Ser. No. 483,992, Feb. 22, 1990, abandoned, which is a continuation of Ser. No. 28,272, Mar. 20, 1987, abandoned.

[30] Foreign Application Priority Data

Mar. 21, 1986 [GB] United Kingdom ............... 8607137

[51] Int. Cl.$^5$ ............... A61K 33/26; A61K 31/295; A61K 31/20; A61K 31/70
[52] U.S. Cl. ............... 424/646; 424/647; 424/648; 514/502; 514/560; 514/23
[58] Field of Search ............... 514/560, 549, 502, 23; 424/646, 647, 648

[56] References Cited

U.S. PATENT DOCUMENTS

| | | | |
|---|---|---|---|
| 3,911,117 | 10/1975 | Ender | 514/502 |
| 4,526,902 | 7/1985 | Rubin | 514/560 |
| 4,681,896 | 7/1987 | Horrobin | 514/861 |
| 4,703,060 | 10/1987 | Traitler et al. | |
| 4,745,099 | 5/1988 | Akamatsu | 514/814 |

OTHER PUBLICATIONS

*Chemotherapy of Cancer*, 2nd edition (1981) Carter et al. Appendix C, pp. 361–365.
Current Medical Diagnosis & Treatment Krupp et al 1976 pp. 940–941.
The Merck Manual, 1982 14th ed p. 2443.
Chem Abstracts 91(1):9491x p. 279 Jul. 2, 1979 (I).
Chem Abstracts 84(12):79729k p. 392 Mar. 22, 1976 (II).
Clinical Toxicology of Commercial Products Acute Poisoning Gleason et al. 3rd edition 1969.

*Primary Examiner*—Frederick E. Waddell
*Assistant Examiner*—Raymond J. Henley, III
*Attorney, Agent, or Firm*—Nixon & Vanderhye

[57] ABSTRACT

Pharmaceutically acceptable compositions of one or more n-6 or n-3 essential fatty acids, particularly gamma-linolenic acid, dihomo-gamma-linolenic acid, or eicosapentaenoic acid, and assimilable iron compounds, in dosage unit form optionally with a diluent or carrier, said acids being present as such or as derivatives convertible in the body thereto and the amounts of said acids or derivatives being 1 mg to 100 g (calculated as gamma-linolenic acid) and of said iron compounds 0.1 mg to 10 g (calculated as iron) or submultiples of said amounts convenient for daily administration thereof.

4 Claims, No Drawings

IRON-CONTAINING COMPOSITIONS AND METHOD FOR TREATING CANCER

This is a continuation of application Ser. No. 07/483,992, filed Feb. 22, 1990 now abandoned, which is a continuation of application Ser. No. 07/028,272, filed Mar. 20, 1987, now abandoned.

FIELD OF INVENTION

The invention relates to iron-containing compositions and methods for the treatment of cancer.

PUBLISHED PATENT APPLICATIONS AND GENERAL LITERATURE

In previous Patent Applications of the inventor the role of essential fatty acids in cancer, and particularly of gamma-linolenic acid and dihomo-gamma-linolenic acid, has been discussed and especially in relation to prostaglandin (PG) metabolism. Such cases include European Patent Application No. 79300546.3 published as Specification No. 0 004 770, covering both cancer and a variety of inflammatory disorders where colchicine and a number of other materials are used with the gamma- and dihomo-gamma-linolenic acids; European Patent Application No. 81300867.9 published specification No. 0 037 175 where the use against cancer of the reverse transformer thioproline with the gamma- and dihomo-gamma-linolenic acid is discussed; and European Patent Application No. 83300622.4 published as Specification No. 0 087 865 where the use against cancer of glutathione and optionally also reverse transformers is discussed.

Further there have been a number of publication in which the effect of polyunsaturated fatty acids alone on cancer cell lines has been discussed, of which Begin et al Prostaglandins Leukotrienes and Medicine 19 177–180 (1985) is an example, as well as clinical reports on their effect on terminal human cancer such as van der Merve S.A. Med. J. 65 712 (5 May 1984). Further in previous Patent Applications of the inventor specific fatty acid combinations have been proposed for the treatment of a number of conditions including cancer, specifically compositions of delta-7,10,13,16-docosatetraenoic acid in European Patent Application No. 84304610.3 published as Specification No. 0 132 089 and compositions of one or more of the metabolites of linoleic acid (gamma-linolenic acid and higher acids related to it) and alpha-linolenic acid (delta6,9,12,15,-octadecatetraenoic acid and higher acids related to it).

DISCUSSION OF BACKGROUND

All this material may be referred to for the background but briefly it is in two parts. The first is that considerable interest has been shown in recent years in the use of prostaglandin (PG) precursors in medicine.

For various reasons when raised levels of prostaglandins are required it is not usually practical to administer naturally occurring prostaglandins such as PGE1 and PGE2 to patients. Consequently, considerable attention has focussed on the use of prostaglandin precursors including linolenic acid, gamma-linoleic acid (GLA) and dihomo-gamma-linolenic acid (DGLA).

Conversion of these materials in the body is believed to be as shown in the following diagram:

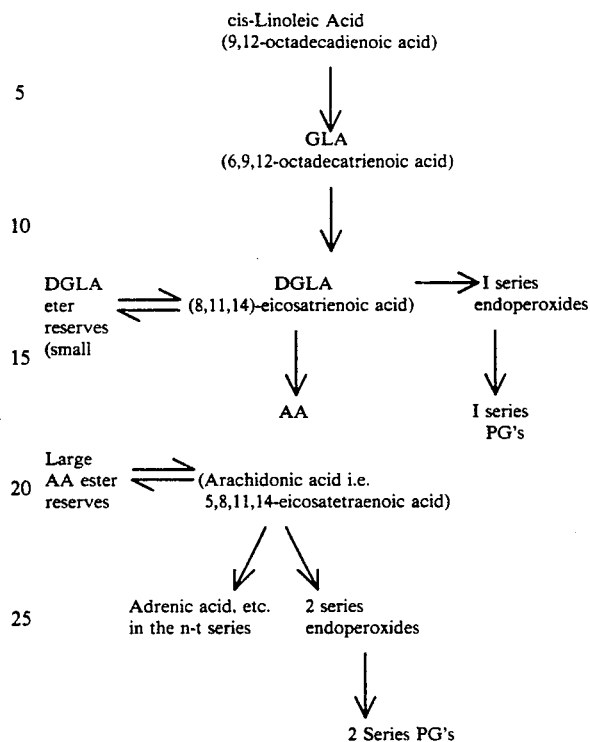

The broad outline of this pathway is well known, and it brings out clearly that a major function of essential fatty acids (EFAs) is to act as precursors for prostaglandins, 1-series PGs being formed from dihomogamma-linolenic acid (DGLA) and 2-series PGs from arachidonic acid (AA). DGLA and AA are present in food in only small quantities, and the major EFA in food is linoleic acid which is first converted to gamma-linolenic acid (GLA) and then to DGLA and AA, the latter step being irreversible. The conversion of linoleic acid to GLA is a limiting step, adequate in the young and healthy body but often inadequate in ageing or in many diseased states.

DGLA is the key substance. GLA is almost completely and very rapidly converted in the body to DGLA and so for practical purposes the oral administration of DGLA and GLA amounts to the same thing. DGLA can be converted to a storage form, changed to arachidonic acid and thence to PGs of the 2-series, or converted to PGs of the 1-series.

One particular characteristic shown by human and animal cancer cells and by transformed cells is a consistent absence of the enzyme delta-6-desaturase which converts linoleic acid to gamma-linolenic acid. The inventor believes that this fact is of great significance and that faulty essential fatty acid metabolism is a key factor in cancer.

The outline of the pathways of EFA metabolism in the body is as above, and as stated DGLA is the key substance. It can be converted to a storage form, or to PGs of the 1-series, or to arachidonic acid and thence to PGs of the 2-series. The conversion to arachidonic acid is irreversible.

Accordingly, it can be seen that since gamma-linolenic acid is a necessary precursor of dihomo-gamma-linolenic acid and thus of 1-series PGs, and since also cellular stores of DGLA are very limited, cancer cells and transformed cells soon lose the ability to make 1-series PGs and in particular the important compound PGE1.

The inventor believes that many of the characteristic features of transformed and cancer cells are due to this damage to PG metabolism and accordingly that measures used in the treatment of cancer will be more effective, particularly in the long term, if they are supported by measures to restore production of 1-series PGs and particularly PGE1 in the cells.

EFAs GENERALLY

The second part of the background is increasing awareness of the significance of the essential fatty acids in themselves, in which considerable general interest has been shown in recent years, primarily in as such and in relation to prostaglandin metabolism, but the acids of the n-6 series both also in the acids of the n-3 series. The n-6 acids in particular are required in the body for the structure of membranes in and around cells, being believed to be necessary for maintaining normal flexibility, fluidity and permeability of such membranes and while less is known of the role of the n-3 series acids they are, equally, present.

The pathways of metabolism of the n-6 essential fatty acids and the related n-3 acids sharing, it is believed, common enzymes in the two pathways, are:

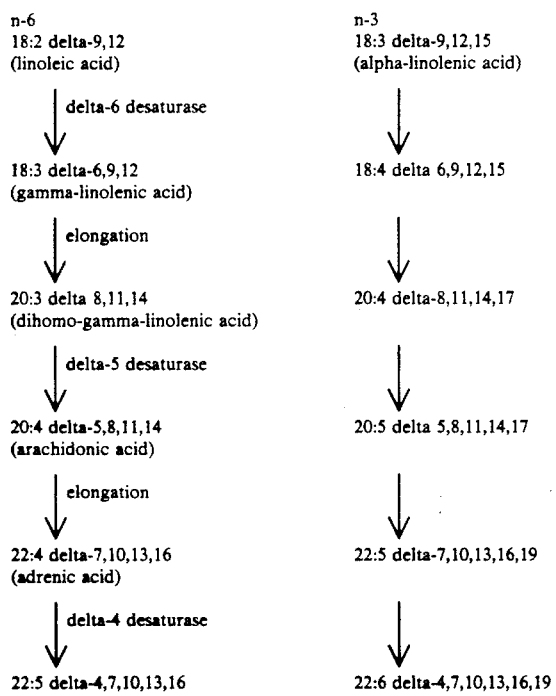

The pathways are not normally reversible nor, in man, are n-3 and n-6 series acids interconvertible.

The acids, which naturally are of the all-cis configuration, are systematically named as derivatives of the corresponding octadeconoic, eicosanoic or docosanoic acids e.g. delta-9,12-octadecadienoic acid or delta-4,7,10,13,16,19-docosahexaenoic acid, but numerical designation such as, correspondingly, 18:2 n-6 or 22:6 n-3 is convenient. Initials, for example, DHA for 22:6 n-3 (docosa hexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature is to the alpha-acid.

In the body, the n-3 acids are metabolised preferentially and as a result, in plasma for example, levels of alpha-linolenic acid (18:3 n-3) are low and 18:4 n-3 and 20:4 n-3 are in trace amounts only. In contrast the n-6 acids are normally present in moderate amounts, though gamma-linolenic acid (GLA) is at low levels, being apparently converted to dihomo-gamma-linolenic acid (DGLA) more rapidly than its relatively slow production from linoleic acid. In both series the elongation stages in the metabolic pathways are much more rapid that the desaturations.

Generally, as appears from the earlier patent applications referred to, and from other publications by the inventor, the actions of the 1-series PGs and other metabolic products derived from DGLA are almost all either desirable or neutral, but the actions of the 2-series PGs and other metabolic products derived from arachidonic acid are very mixed, some being desirable and some being highly undesirable. Studies of the interactions between the metabolism of the n-6 acids and that of the n-3 acids have shown that elongation reactions (eg GLA to DGLA) are highly efficient and there is very little competition either way. In contrast, the two series of fatty acids are in competition in the desaturation processes. The n-3 fatty acids interfere with both delta-6 and delta-5 desaturation in the n-6 series. This competition seems to occur even when the n-3 fatty acid is not actually a substrate for the enzyme concerned. For example, 20:5 n-3 competitively inhibits the delta-6 desaturation forming GLA from linoleic acid and overall the presence of n-3 fatty acids in a combination leads to some inhibition of the conversion of DGLA to arachidonic acid by the delta-5 desaturase. Thus, as one example of the interrelations, as a result of the presence of n-3 EFAs, the efficiency of either GLA or DGLA in increasing the ratio of DGLA products (1-series PGs) to arachidonic acid products (2-series PGs) will be increased.

It must be emphasised that while the prostaglandins are important, the EFA molecules themselves have many biological actions, and also have effects as a result of conversion to products other than prostaglandins, including products of lipoxygenase enzyme activities. When considering the effects of GLA and other EFAs, it is essential to appreciate that some of the desirable effects may relate to actions of the unmetabolised fatty acids themselves and to metabolites other than PGs. The invention relates to the administration of the EFAs and is not restricted to action of those EFAs which are dependent on formation of prostaglandins.

DISCOVERY BEHIND PRESENT INVENTION

Using a human breast cancer cell line (ZR-75-11) from the American Type Culture Collection we have found that the cancer cell killing effect of fatty acids is dramatically enhanced when the fatty acids are provided to cancer cells in the presence of iron. Breast cancer cells were cultured as described by Begin et al and at the end of seven days the percentages of dead cells were estimated. Initial experiments were performed using a GLA concentration of 10 microgram/ml, a concentration which usually kills in the region of 50% of these cells at the end of 7 days culture. Iron in various forms was added to the culture medium and it was found that in the presence of iron in excess of 90% of the cancer cells were killed by the end of seven days, an effect normally achieved only by GLA concentrations of 20 microgram/ml. A variety of iron compounds was tested and while there were some small differences in potency between them, the presence of iron itself seemed to be the critical factor. Ferric chloride, ferrous sulphate, ferric acetate, ferrous citrate and the iron complex of the porphyrin compounds such as mesoporphyrins with each of the carbons bridging the heterocyclic rings substituted with a paraphenyl group were all effective in enhancing the cell-killing effect of GLA. As with GLA itself, normal cell lines such as human fibroblasts and canine kidney cells, were unaffected by the iron/GLA combination.

The cancer cell killing action of DGLA, AA and EPA (20:5 n-3) were also enhanced in a similar way by iron containing compounds. Moreover, the effects were also apparent in other human lung and prostate cancer cell lines. We therefore conclude that the potentiating effect is a general one in that it applies to all the iron compounds we have tried, all the essential fatty acids which have been shown to have selective effects on cancer cells, which besides the above includes linoleic acid, alpha-linolenic acid and DHA (22:6 n-3), and a variety of different types of cancer cell line taken from humans.

THE INVENTION

The invention therefore lies in the preparation of compositions for and methods of treatment of cancer in which one or more of the n-6 or n-3 essential fatty acids, preferably GLA, DGLA or EPA, are administered in daily doses of 1 mg to 100 g (preferably 50 mg to 10 g) together with an iron containing compound which provides a daily dose of 0.1 mg to 10 g of assimilable iron (preferably 5 mg to 500 mg). The fatty acid may be administered by any appropriate route, eg. oral, parenteral or topical which delivers the fatty acid to the cancer cells. Similarly the iron may be delivered by any appropriate route, not necessarily the same one used to administer the fatty acid. The daily dose does not exclude the administration of long acting or depot preparation in which the daily dose is delivered by administration of such a depot preparation once a week, once a month, or at some other appropriate time interval. The fatty acids may be present in any physiologically assimilable form, including glycerides, esters, amides, phospholipids or free acids.

Equally the invention lies in the use GLA, or other n-6 or n-3 EFAs as such or in other assimilable form and singly or in combinations with each other for the manufacture of a medicament for use in such treatment, as well as per se novel compositions with assimilable iron compounds.

FORMS AND SOURCES OF THE ACIDS

The acids may be used as such or as pharmaceutically acceptable and physiologically equivalent derivatives as. for example, detailed below for gamma-linolenic acid and dihomo-gamma-linolenic acid, and reference to any of the acids is to be taken as including reference to the acids when in the form of such derivatives. Equivalence is demonstrated by entry into the pathways quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemist Society, Champaign, Ill., U.S.A.

Convenient physiologically equivalent derivatives of gamma-linolenic acid and dihomo-gamma-linolenic acid include salts, amides, esters including glyceride esters and alkyl (e.g. C1 to C4) esters, and phospholipids.

If desired, pharmaceutical compositions may be produced for use in the invention by associating the natural or synthetic acids, as such or as derivatives, with an acceptable pharmaceutical vehicle. It is, however, at present convenient to incorporate at least the gamma-linolenic acid into compositions in the form of an available oil having a high gamma-linolenic acid content, hence references to "oil" herein.

At the present time known natural sources or oils having a high gamma-linolenic acid content are few (there are no known natural sources of significant amounts of dihomo-gamma-linolenic acid). One source of oils currently available is the seed of Evening Primrose species such as *Oenothera biennis L.* and *Oenothera lamarckiana*, the oil extract therefrom containing gamma-linolenic acid (about 8%) and linoleic acid (about 72%) in the form of their glycerides together with other glycerides (percentages based on total fatty acids). Other sources of gamma-linolenic acid are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic as the main fatty acid components, the gamma-linolenic and linoleic as the main fatty acid components, the gamma-linolenic acid content being if desired a major proportion. Seed oil extracts appear to have a stabilising effect upon dihomo-gamma-linolenic acid if present.

Natural sources of 22:4 and 22:5 n-6 acids include adrenal glands 22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

Advantageously, a preservative is incorporated into the preparations: alpha-tocopherol in concentration of about 0.1% by weight has been found suitable for the purpose.

EXAMPLES

A. Soft or hard gelatine capsules made by conventional methods are administered to persons suffering from cancer in conjunction with iron tablets as follows:

1. 500 mg capsules of Evening Primrose Oil containing 45 mg GLA, six to fifty per day, in conjunction with 2-10 iron tablets each providing 5 mg of elemental iron in the form of ferrous fumarate, ferrous gluconate or ferrous sulphate.

2. 500 mg capsules of borage oil containing 90 mg of GLA, 4 to 40 per day, in conjunction with 2-10 iron tablets per day each providing 5 mg of elemental iron in said form.

3. Capsules containing 500 mg of GLA as a concentrate of Evening Primrose Oil, borage oil or fungal oil, 4 to 20 per day, in conjunction with 1-10 iron tablets per day each providing 10 mg of iron in said form.

4 Capsules containing 200 mg pure dihomo-gamma-linolenic acid, 5-30 per day, with 1-10 iron tablets per day each providing 10 mg of iron in said form.

5. Capsules containing 100 mg GLA, 20 mg of arachidonic acid and 50 mg of EPA, 4-40 per day, in conjunction with 1-10 iron tablets per day, each providing 10 mg of elemental iron in said form.

6. Capsules containing 200 mg GLA, 100 mg DGLA, 50 mg 22:4 n-6, 50 mg 20:5 n-3 and 50 mg 22:6 n-3, in conjunction with 2-10 iron tablets per day, each providing 5 mg of elemental iron in said form.

B. Soft or hard gelatine capsules made by conventional methods, in which the fatty acids and the iron in the forms and to give the daily doses as above are incorporated together into the same capsules, are administered to persons suffering from cancer.

C. Intravenous preparations of fatty acids in which appropriate daily doses as above are give by intravenous administration of fatty acid emulsions, are coupled with daily doses as above of iron given either in the same preparation or by another route, for example, iron-dextran or iron-sorbitol preparations for intramuscular injection, in the treatment of persons suffering from cancer.

D. Topical preparations of fatty acids in which daily doses as above are applied to primary or metastatic human skin cancers topically, accompanied by iron either topically in the same preparation or by another, systemic route.

We claim:

1. A method of treating cancers sensitive to treatment with the combination of gamma-linolenic acid or dihomo-gamma-linolenic acid or both in an amount of 1 mg of 100 g daily and an assimilable iron compound capable of damaging cancer cells in an amount of 0.1 mg to 1 g (calculated as iron) daily comprising administering to a person requiring such treatment said combination of gamma-linolenic acid, dihomo-gamma-linolenic acid of both, as such or as the molar equivalent amount of a compound convertible in the body thereto, and said iron compound, wherein the weight ratio of said fatty acid component to said iron component is about 1:2.

2. The method according to claim 1, in which the amounts of said iron are 5 mg to 500 mg and of said acid is 50 mg to 10 g daily.

3. The method according to claim 1 or 2, wherein said essential fatty acid is selected from the group consisting of gamma-linolenic acid, dihomo-gamma-linolenic acid and eicosapentanoic acid.

4. A method of treating cancers sensitive to treatment with an essential fatty acid selected from gamma-linolenic acid, dihomo-gamma-linolenic acid, 20:5 delta-5,8,11,14,17 eicosapentaenoic acid and 2:6 delta-4,7,10,13,16,19 docosahexaenoic acid or combinations thereof in an amount of 1 mg to 100 g daily and an assimilable iron compound capable of damaging cancer cells in an amount of 0.1 mg to 1 g (calculated as iron) daily, comprising administering to a person requiring such treatment said combination of selected essential fatty acid(s) as such or as the molar equivalent amount of compound(s) convertible in the body thereto, and said iron compound, wherein the weight ratio of said fatty acid component to said iron component of about 1:2.

* * * * *